ns011206998B2

United States Patent
Lee

(10) Patent No.: US 11,206,998 B2
(45) Date of Patent: *Dec. 28, 2021

(54) OPTICAL TRACKING SYSTEM FOR TRACKING A PATIENT AND A SURGICAL INSTRUMENT WITH A REFERENCE MARKER AND SHAPE MEASUREMENT DEVICE VIA COORDINATE TRANSFORMATION

(71) Applicant: KOH YOUNG TECHNOLOGY INC., Seoul (KR)

(72) Inventor: Hyun Ki Lee, Daegu (KR)

(73) Assignee: KOH YOUNG TECHNOLOGY INC., Seoul (KR)

(*) Notice: Subject to any disclaimer, the term of this patent is extended or adjusted under 35 U.S.C. 154(b) by 1240 days.

This patent is subject to a terminal disclaimer.

(21) Appl. No.: 15/512,273

(22) PCT Filed: Sep. 18, 2015

(86) PCT No.: PCT/KR2015/009842
§ 371 (c)(1),
(2) Date: Mar. 17, 2017

(87) PCT Pub. No.: WO2016/043560
PCT Pub. Date: Mar. 24, 2016

(65) Prior Publication Data
US 2017/0273595 A1    Sep. 28, 2017

(30) Foreign Application Priority Data
Sep. 19, 2014  (KR) .................. 10-2014-0125204

(51) Int. Cl.
*A61B 5/06* (2006.01)
*A61B 34/20* (2016.01)
(Continued)

(52) U.S. Cl.
CPC ............ *A61B 5/06* (2013.01); *A61B 34/20* (2016.02); *A61B 90/36* (2016.02); *G01B 11/002* (2013.01);
(Continued)

(58) Field of Classification Search
CPC ............ A61B 34/20; A61B 2090/365; A61B 2034/2055; A61B 2034/2068; A61B 2090/371; G01B 11/002
See application file for complete search history.

(56) References Cited

U.S. PATENT DOCUMENTS

2004/0249266 A1    12/2004   Friedrich et al.
2007/0019936 A1    1/2007    Birkenbach et al.
(Continued)

FOREIGN PATENT DOCUMENTS

CN    101019771    8/2007
CN    101222882    7/2008
(Continued)

OTHER PUBLICATIONS

European Office Action, corresponding to European Application No. 15 843 042.1, dated Feb. 14, 2020.
(Continued)

*Primary Examiner* — Serkan Akar
(74) *Attorney, Agent, or Firm* — Kile Park Reed & Houtteman PLLC

(57) ABSTRACT

An optical tracking system may comprise a reference marker unit stationarily disposed relative to a patient, a shape measurement unit configured to measure the three-dimensional shape of a specified part of the patient corresponding to a three-dimensional image, a tracking sensor unit configured to sense the reference marker unit and the shape measurement unit, and a processing unit. The processing unit may acquire a coordinate transformation relationship
(Continued)

between the reference marker unit and the tracking sensor unit and a coordinate transformation relationship between the shape measurement unit and the tracking sensor unit based on a sensing result of the tracking sensor unit, acquire a coordinate transformation relationship between the specified part of the patient and the shape measurement unit based on a measurement result of the shape measurement unit, and define a coordinate system of the patient relative to the reference marker unit from the acquired coordinate transformation relationships.

7 Claims, 4 Drawing Sheets

(51) Int. Cl.
G06T 7/292 (2017.01)
A61B 90/00 (2016.01)
G01B 11/00 (2006.01)

(52) U.S. Cl.
CPC ...... G06T 7/292 (2017.01); A61B 2034/2046 (2016.02); A61B 2034/2055 (2016.02); A61B 2034/2057 (2016.02); A61B 2034/2068 (2016.02); A61B 2090/365 (2016.02); A61B 2090/373 (2016.02)

(56) References Cited

U.S. PATENT DOCUMENTS

| 2007/0034731 | A1* | 2/2007 | Falco | A61B 34/20 244/3.1 |
|---|---|---|---|---|
| 2007/0270690 | A1 | 11/2007 | Woerlein | |
| 2011/0054300 | A1 | 3/2011 | Yamamoto et al. | |
| 2011/0270084 | A1 | 11/2011 | Choi et al. | |
| 2012/0082342 | A1 | 4/2012 | Kim et al. | |
| 2013/0060146 | A1 | 3/2013 | Yang et al. | |
| 2013/0108979 | A1 | 5/2013 | Daon | |
| 2013/0131504 | A1 | 5/2013 | Daon | |
| 2013/0131505 | A1 | 5/2013 | Daon et al. | |
| 2014/0228675 | A1 | 8/2014 | Daon | |
| 2015/0287236 | A1* | 10/2015 | Winne | G06T 15/08 |
| 2015/0302590 | A1 | 10/2015 | Hong | |

FOREIGN PATENT DOCUMENTS

| CN | 102999902 | 3/2013 |
|---|---|---|
| JP | 2006-526433 | 11/2006 |
| KR | 10-0961661 | 6/2010 |
| KR | 10-1049507 | 7/2011 |
| KR | 10-2012-0035021 | 4/2012 |
| KR | 10-2014-0088167 | 7/2014 |
| WO | 2006/124388 | 11/2006 |
| WO | 2007/091464 | 8/2007 |
| WO | 2012/129229 | 9/2012 |
| WO | 2014/068106 | 5/2014 |
| WO | 2014/109520 | 7/2014 |

OTHER PUBLICATIONS

Indian Office Action, with English translation, corresponding to Application No. 201717013266, dated Nov. 11, 2019.
Chinese Office Action with English translation corresponding to Chinese Application or Publication No. 201580050352.0, dated Aug. 2, 2019.
Chinese Office Action with English translation for Chinese Application No. 201580050352, dated Nov. 21, 2018.
European Office Action for European Application No. 15 843 042.1, dated Jun. 11, 2019.
International Search Report for International Application No. PCT/KR2015/009842, dated Dec. 17, 2015.
European Office Action, corresponding to European Application No. 15 843 042.1, dated Oct. 9, 2020.
Jason Geng, "Structured-light 3D surface imaging: a tutorial", IEEE Intelligent Transportation System Society, Advances in Optics and Photonics; Mar. 31, 2011, pp. 128-160.
Wikipedia; "A structured-light 3D scanner"; https://en.wikipedia.org/w/index.php?title=Structured-light_3D_scanner&oldid=618287759; Jul. 24, 2014; Borko Furht, "Encyclopedia of Multimedia (2nd ed.)", Springer, p. 222, ISBN 978-0-387-74724-8. 2008.
Wikipedia "3D scanning" https://en.wikipedia.org/w/index.php?title=3D_scanning&oldid=623736578; Sep. 1, 2014; pp. 1-11.

* cited by examiner

# OPTICAL TRACKING SYSTEM FOR TRACKING A PATIENT AND A SURGICAL INSTRUMENT WITH A REFERENCE MARKER AND SHAPE MEASUREMENT DEVICE VIA COORDINATE TRANSFORMATION

TECHNICAL FIELD

The present disclosure relates to an optical tracking system and a coordinate registration method for an optical tracking system and, more particularly, to an optical tracking system for tracking a patient or a surgical instrument and a coordinate registration method for an optical tracking system for tracking a patient or a surgical instrument.

The present disclosure was derived from studies carried out as part of the industrial source technology development project of the Ministry of Knowledge Economy of Republic of Korea [Assignment specific number: 10040097, Assignment name: Development of technology on minimally-invasive multiple-degree-of-freedom surgical robot system for medical surgical robot video-based otolaryngology operation and neurosurgery operation].

BACKGROUND ART

Recently, in a surgery for treating a lesion of a patient, an image-guided surgery using a pre-captured image is widely utilized. In particular, when a surgery is to be performed while avoiding important nerves and major organs in a patient's body, high accuracy is required in performing the surgery on the basis of images captured in advance.

In general, images captured in advance include three-dimensional images obtained by MRI imaging, CT imaging, or the like. At the time of starting a surgery, it is necessary to perform registration by which a coordinate system of such three-dimensional images captured in advance and a coordinate system of a patient are matched with each other. While the surgery is in progress, it is necessary to determine in real time a change in position and posture according to a movement of the patient and a surgical instrument. In addition, when the posture of the patient is changed during the surgery, there is a need to perform re-registration of a coordinate system of the patient to continuously track the patient or a lesion.

In the related art, a dynamic reference base (DRB) has been used for such registration and tracking. That is, after the DRB is attached to a patient in advance, a three-dimensional image such as CT or the like is captured and at the time of starting a surgery, a coordinate system of the three-dimensional image and a coordinate system of the patient are registered with each other. While the surgery is in progress, a surgical instrument is tracked based on the DRB, thereby tracking the position or the like of the surgical instrument relative to a lesion of the patient. In this case, for the purpose of registration, it is necessary to capture a three-dimensional image in advance while keeping the DRB fixed to the patient. For accurate tracking, it is necessary to strictly fix the DRB to the patient.

To this end, in the related art, several methods have been adopted such as a method for sensing and tracking a marker after implanting the marker in a bone of a patient, a method for sensing and tracking a template to which a marker is attached by having a patient bite the template with his or her teeth, and a method using a STAMP (Surface Template-Assisted Marker Position) processed by generating an artificial structure.

However, the conventional methods above suffer from a variety of problems such as the difficulty involved in attaching the marker, side effects caused by implanting the marker in the bone, a reduction in accuracy and reliability attributable to the change in the marker position which may be generated when the marker is bitten by teeth, inconvenience in manufacturing an expensive STAMP before a surgery and the substantial time and cost required for manufacturing the STAMP, etc. Moreover, in the case of the conventional methods, even when the DRB is strictly fixed to a patient, if the patient moves, the distance between the DRB and the lesion of the patient or the posture of the patient may change. Thus, accurate tracking cannot be carried out and re-registration cannot be performed, thereby resulting in a problem that the DRB cannot be used. Accordingly, in the case of the conventional methods, a surgery is performed under the assumption that the patient does not move. In practice, however, it is often the case that a patient moves during a surgery. Thus, it is difficult to carry out the tracking in a substantially accurate manner.

Accordingly, there is a need to develop a registration method capable of acquiring an accurate registration result in a shorter time and with a reduced cost. Further, there is a need to develop a tracking system and tracking method in which tracking is performed in a relatively accurate and easy manner even if a patient moves or the posture of the patent changes during a surgery.

SUMMARY

Accordingly, it is an object of the present disclosure to provide an optical tracking system capable of accurately and easily tracking a patient or a surgical instrument in a shorter time and with a reduced cost.

Another object of the present disclosure is to provide a coordinate registration method for an optical tracking system capable of accurately and easily tracking a patient or a surgical instrument in a shorter time and with a reduced cost.

According to one exemplary embodiment of the present disclosure, an optical tracking system is provided for tracking a patient or a surgical instrument for surgically treating the patient, by using a three-dimensional image acquired in advance before surgical treatment for the patient. The optical tracking system includes a reference marker unit, a shape measurement unit, a tracking sensor unit, and a processing unit. The reference marker unit is stationarily disposed relative to the patient. The shape measurement unit is configured to measure a three-dimensional shape of a specified part of the patient corresponding to the three-dimensional image. The tracking sensor unit is configured to sense the reference marker unit and the shape measurement unit so as to track the reference marker unit and the shape measurement unit, respectively. The processing unit is configured to acquire a coordinate transformation relationship between the reference marker unit and the tracking sensor unit and a coordinate transformation relationship between the shape measurement unit and the tracking sensor unit based on a sensing result of the tracking sensor unit, to acquire a coordinate transformation relationship between the specified part of the patient and the shape measurement unit based on a measurement result of the shape measurement unit, and to define a coordinate system of the patient relative to the reference marker unit from the acquired coordinate transformation relationships.

In one embodiment, the shape measurement unit may include a measurement device, which measures the three-dimensional shape of the specified part of the patient corresponding to the three-dimensional image, and a marker installed on the measurement device, and the tracking sensor unit may be configured to sense the marker of the shape measurement unit. The processing unit may be configured to acquire a coordinate transformation relationship between the marker of the shape measurement unit and the tracking sensor unit and a coordinate transformation relationship between the measurement device and the marker of the shape measurement unit.

For example, the coordinate transformation relationships may be expressed as coordinate transformation matrices, and the processing unit may be configured to define the coordinate system of the patient relative to the reference marker unit according to the following mathematical formula:

$$PR = T1^{-1} T2 T3 T4$$

where PR is a coordinate transformation matrix of the patient with respect to the reference marker unit, T1 is a coordinate transformation matrix of the reference marker unit with respect to the tracking sensor unit, T2 is a coordinate transformation matrix of the marker of the shape measurement unit with respect to the tracking sensor unit, T3 is a coordinate transformation matrix of the measurement device with respect to the marker of the shape measurement unit, and T4 is a coordinate transformation matrix of the patient with respect to the measurement device of the shape measurement unit.

For example, the tracking sensor unit may be configured to measure information for acquiring the coordinate transformation matrix T1 of the reference marker unit with respect to the tracking sensor unit and the coordinate transformation matrix T2 of the marker of the shape measurement unit with respect to the tracking sensor unit, and the shape measurement unit may be configured to measure information for acquiring the coordinate transformation matrix T4 of the patient with respect to the measurement device of the shape measurement unit. The processing unit may be configured to acquire the coordinate transformation matrices T1, T2, and T4 using the measured information and to calculate, from the acquired coordinate transformation matrices T1, T2, and T4, the coordinate transformation matrix T3 of the measurement device with respect to the marker of the shape measurement unit and the coordinate transformation matrix PR of the patient with respect to the reference marker unit. The measurement of the tracking sensor unit and the shape measurement unit may be performed two or more times.

In one embodiment, the processing unit may be configured to register a coordinate system of the three-dimensional image acquired in advance before the surgical treatment for the patient with the coordinate system of the patient relatively defined with respect to the reference marker unit, based on the three-dimensional shape measured in the shape measurement unit.

The optical tracking system may further include a surgical instrument including a marker and configured to surgically treat the patient. The tracking sensor unit may be configured to sense the marker of the surgical instrument so as to track the marker of the surgical instrument, and the processing unit may be configured to acquire a coordinate transformation relationship between the reference marker unit and the tracking sensor unit and a coordinate transformation relationship between the marker of the surgical instrument and the tracking sensor unit based on a sensing result of the tracking sensor unit and to define a coordinate system of the surgical instrument relative to the patient by using the acquired coordinate transformation relationships and the coordinate system of the patient relatively defined with respect to the reference marker unit.

In one embodiment, the processing unit may be configured to register the coordinate system of the three-dimensional image acquired in advance before the surgical treatment for the patient with the coordinate system of the surgical instrument relatively defined with respect to the patient, based on a registration result of the coordinate system of the three-dimensional image and the coordinate system of the patient.

The processing unit may be configured to automatically or manually re-define the coordinate system of the patient when the patient moves.

According to another exemplary embodiment of the present disclosure, a coordinate registration method for an optical tracking system includes: acquiring a three-dimensional image of a patient before surgical treatment for the patient; sensing, by a tracking sensor unit, a reference marker unit stationarily disposed relative to the patient and a shape measurement unit configured to measure a three-dimensional shape of a specified part of the patient corresponding to the three-dimensional image; acquiring a coordinate transformation relationship between the reference marker unit and the tracking sensor unit and a coordinate transformation relationship between the shape measurement unit and the tracking sensor unit based on a sensing result of the tracking sensor unit, and acquiring a coordinate transformation relationship between the specified part of the patient and the shape measurement unit based on a measurement result of the shape measurement unit; and defining a coordinate system of the patient relative to the reference marker unit from the acquired coordinate transformation relationships.

In one embodiment, acquiring the coordinate transformation relationship between the reference marker unit and the tracking sensor unit and the coordinate transformation relationship between the shape measurement unit and the tracking sensor unit, and the acquiring the coordinate transformation relationship between the specified part of the patient and the shape measurement unit may include: acquiring a coordinate transformation relationship between the reference marker unit and the tracking sensor unit and a coordinate transformation relationship between a marker of the shape measurement unit and the tracking sensor unit; acquiring a coordinate transformation relationship between a measurement device of the shape measurement unit and the marker of the shape measurement unit; and acquiring a coordinate transformation relationship between the patient and the measurement device of the shape measurement unit.

The coordinate registration method for an optical tracking system may further include: after the defining the coordinate system of the patient relative to the reference marker unit from the acquired coordinate transformation relationships, registering a coordinate system of the acquired three-dimensional image with the defined coordinate system of the patient based on the three-dimensional shape measured in the shape measurement unit.

The coordinate registration method for an optical tracking system may further include: after registering the coordinate system of the acquired three-dimensional image with the defined coordinate system of the patient, sensing, by the tracking sensor unit, a marker of a surgical instrument for surgically treating the patient; acquiring a coordinate transformation relationship between the reference marker unit and the tracking sensor unit and a coordinate transformation relationship between the marker of the surgical instrument and the tracking sensor unit based on a sensing result of the tracking sensor unit; and defining a coordinate system of the surgical instrument relative to the patient by using the acquired coordinate transformation relationships and the coordinate system of the patient relatively defined with respect to the reference marker unit.

The coordinate registration method for an optical tracking system may further include: after defining the coordinate system of the surgical instrument relative to the patient, registering the coordinate system of the acquired three-dimensional image with the defined coordinate system of the surgical instrument based on a registration result of the coordinate system of the three-dimensional image and the coordinate system of the patient.

When the patient moves, the step of sensing, by the tracking sensor unit, the reference marker unit stationarily disposed relative to the patient and the shape measurement unit configured to measure the three-dimensional shape of the specified part of the patient corresponding to the three-dimensional image and the subsequent steps may be performed repeatedly.

According to the present disclosure, the optical tracking system includes the shape measurement unit configured to measure a three-dimensional shape of a specified part of a patient. The shape measurement unit and the reference marker unit are sensed by the tracking sensor unit. Thus, the coordinate system of the patient relative to the reference marker unit can be defined from the coordinate transformation relationships among the shape measurement unit, the reference marker unit, and the tracking sensor unit and during surgical treatment, it is possible to track the patient and the surgical instrument in real time.

Further, the process of defining the coordinate system of the patient relative to the reference marker unit can be re-performed with ease. Therefore, even when the patient moves or the posture of the patient changes, it is possible to accurately reset the coordinate system and accurately track the patient and the surgical instrument in real time.

In addition, registration can be performed using the three-dimensional shape of the patient measured during surgical treatment as a marker. Therefore, even though a DRB is not directly attached to the patient, the coordinate system of the three-dimensional image acquired in advance before surgical treatment can be registered with the coordinate system of the patient and the coordinate system of the surgical instrument, which may move in real time during surgical treatment. Further, even when acquiring the three-dimensional image in advance, the DRB does not need to be attached. Since the resetting and re-registration of the coordinate systems can be performed at any time, it is not necessary to strictly fix the reference marker unit to the patient.

Accordingly, it is possible to solve the problems inherent in the related art, such as the pain experienced by the patient and an error due to directly attaching a marker to the patient, the onerous work of manufacturing the STAMP before a surgery, substantial time and cost required in manufacturing the STAMP, etc.

That is, setting of the coordinate system of the patient and registration of the images can be expeditiously performed in an operating room without a separate preparation process. It is therefore possible to accurately and easily perform the setting of the coordinate system of the patient and the coordinate system of the surgical instrument and the registration of the images in a shorter time and with a reduced cost. Further, the operation to the patient may be performed without the DRB that would otherwise be attached directly to the patient. Thus, it is possible to alleviate the pain of the patient and side effects.

DETAILED DESCRIPTION

Figure 1:
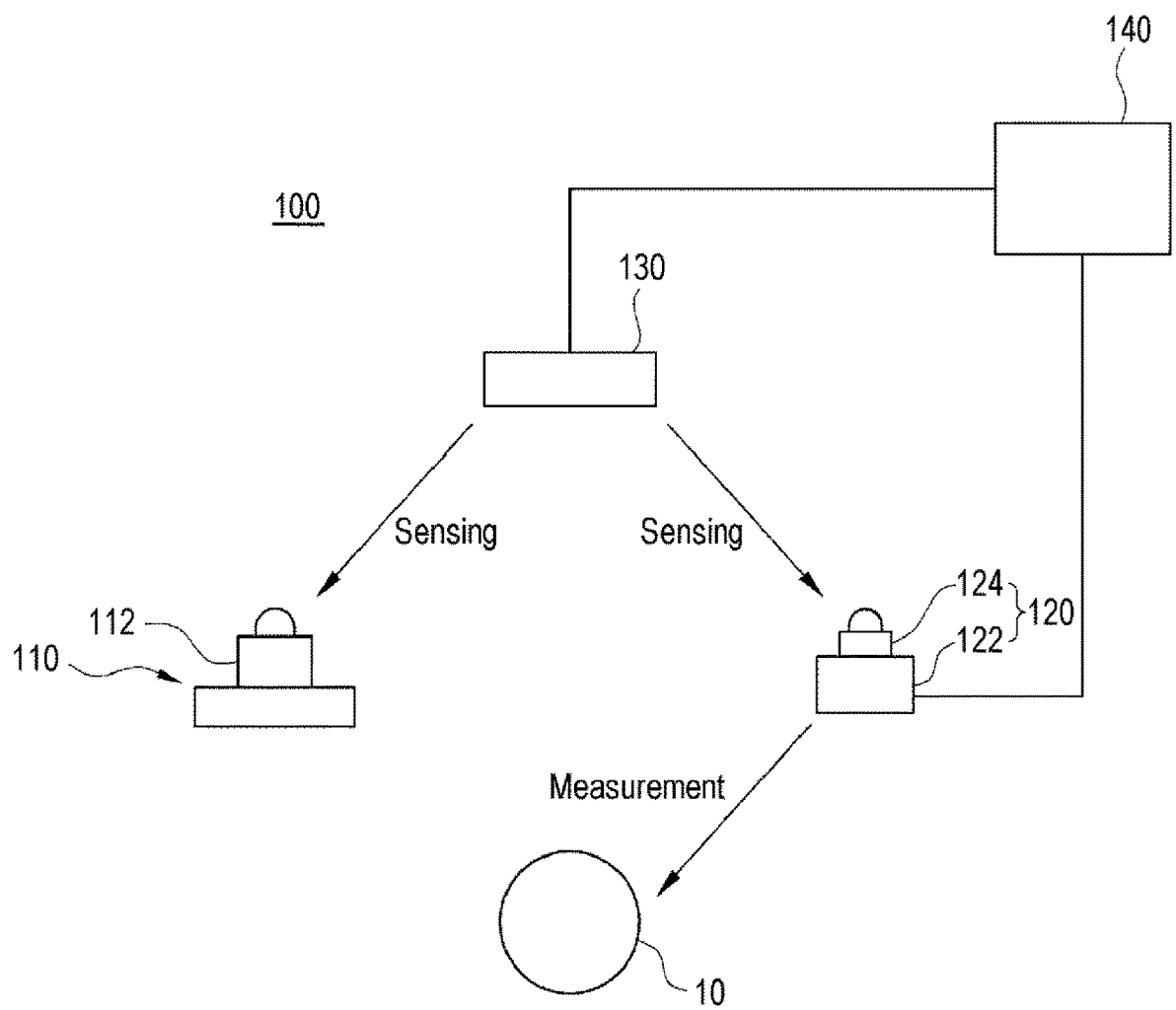
FIG. 1 is a conceptual diagram showing an optical tracking system according to one embodiment of the present disclosure.

The present disclosure may be diversely modified and may have various forms. Specific embodiments will be illustrated in the drawings and will be described in detail. However, this is not intended to limit the present disclosure to specific forms of disclosure. It is to be understood that the present disclosure includes all modifications, equivalents and substitutions which fall within the spirit and technical scope of the present disclosure.

The terms "first" and "second" may be used for describing various components. However, the components shall not be limited by these terms. These terms are used only for the purpose of distinguishing one component from another component. For example, a first component may be named as a second component without departing from the scope of rights of the present disclosure. Similarly, a second component may be named as a first component.

The terms used herein are merely used to describe specific embodiments and are not intended to limit the present disclosure. The singular expression includes plural expressions unless the context clearly indicates otherwise. It should be understood that as used herein, the terms such as "including," "having," and the like are intended to specify the existence of the stated features, numbers, steps, actions, components, parts or combinations thereof and are not intended to preclude in advance the possibility of the existence or addition of one or more other features, numbers, steps, actions, components, parts or combinations thereof.

Unless otherwise defined, all terms used herein, including technical or scientific terms, have the same meanings as generally understood by those having ordinary skill in the art to which the present disclosure belongs.

Commonly used terms such as terms defined in a dictionary or the like are to be interpreted as the meanings consistent with the contextual meanings of the related art. Unless clearly defined herein, such terms are not interpreted in an ideal or overly formal sense.

Preferred embodiments of the present disclosure will now be described in more detail with reference to the accompanying drawings.

FIG. 1 is a conceptual diagram showing an optical tracking system according to one embodiment of the present disclosure.

The optical tracking system according to one embodiment of the present disclosure is provided to track a patient or a surgical instrument for surgically treating the patient, using a three-dimensional image acquired in advance before surgical treatment for the patient.

The three-dimensional image is an image acquired in advance before surgical treatment for the patient 10 and may be utilized as a reference image at the time of surgical treatment for the patient 10. The term "surgical treatment" used herein includes all acts of medical treatment for a patient, including a surgery. For example, the three-dimensional image may include a CT (Computed Tomography) image generally acquired in a hospital for diagnosis and treatment. Alternatively, the three-dimensional image may include other three-dimensional images such as an MRI (Magnetic Resonance Imaging), etc. The three-dimensional image referred to herein is a concept that includes an image obtained by manipulating or reconstructing a directly captured image such as a CT image or the like, and includes both a multi-plane reconstruction image and a three-dimensional reconstruction image that are widely used for actual surgical treatment.

Referring to FIG. 1, the optical tracking system 100 includes a reference marker unit 110, a shape measurement unit 120, a tracking sensor unit 130, and a processing unit 140.

The reference marker unit 110 is stationarily disposed relative to the patient 10.

A marker 112 is installed on the reference marker unit 110. The marker 112 is capable of radiating energy or a signal so that the energy or the signal can be sensed by the tracking sensor unit 130 discussed below. For example, a plurality of markers may be installed on the reference marker unit 110. A single marker having a predetermined pattern may also be installed on the reference marker unit 110.

The reference marker unit 110 corresponds to a conventional DRB. However, the reference marker unit 110 does not serve as a registration reference like the conventional DRB. Therefore, it is not necessary to attach the reference marker unit 110 to the patient 10 when capturing a three-dimensional image such as CT, MRI, or the like. Further, the conventional DRB has to be directly attached to the patient 10 and has to be strictly fixed to the patient 10. In contrast, the reference marker unit 110 may not only be directly attached to the patient 10, but also be merely fixed relative to the patient 10. Thus, the reference marker unit 110 may be attached to a stationary object such as a bed in an operating room or the like and it is not necessary to strictly fix the reference marker unit 110 to the patient 10.

The shape measurement unit 120 is configured to measure a three-dimensional shape for a specified part of the patient 10 corresponding to the three-dimensional image.

In one embodiment, the shape measurement unit 120 may include a measurement device 122 and a marker 124.

The measurement device 122 measures a three-dimensional shape for the specified part of the patient 10 corresponding to the three-dimensional image. In one embodiment, the measurement device 122 may irradiate grid-patterned light on a specified part of the patient 10, acquire a reflective image for the specified part of the patient 10 according to the grid-patterned light, and measure a three-dimensional shape by applying a bucket algorithm to the acquired reflective image. In addition, the measurement device 122 may acquire a three-dimensional image from the measured three-dimensional shape.

The marker 124 is installed on the measurement device 122. The marker 124 may radiate energy or a signal so that the energy or the signal can be sensed by the tracking sensor unit 130 which will be described below. For example, a plurality of markers may be installed on the shape measurement unit 120. A single marker having a predetermined pattern may also be installed on the shape measurement unit 120.

The tracking sensor unit 130 is configured to sense the reference marker unit 110 and the shape measurement unit 120 so as to track each of the reference marker unit 110 and the shape measurement unit 120.

For example, the tracking sensor unit 130 may sense the marker 112 of the reference marker unit 110 and may sense the marker 124 of the shape measurement unit 120. Accordingly, the position and/or the posture of the reference marker unit 110 may be determined and the position and/or the posture of the shape measurement unit 120 may be determined.

The processing unit 140 may include, for example, a computer or a central processing unit of a computer.

The processing unit 140 acquires a coordinate transformation relationship between the reference marker unit 110 and the tracking sensor unit 130 and a coordinate transformation relationship between the shape measurement unit 120 and the tracking sensor unit 130 based on the sensing result of the tracking sensor unit 130. Further, the processing unit 140 acquires a coordinate transformation relationship between the specified part of the patient 10 and the shape measurement unit 120 based on the measurement result of the shape measurement unit 120. Herein, the coordinate transformation relationships may be defined, for example, in the form of matrices.

The processing unit 140 defines a coordinate system of the patient 10 relative to the reference marker unit 110 from the coordinate transformation relationships acquired as above. For example, the coordinate system may be defined in the form of a matrix.

Meanwhile, there is a small difference between the measurement position of the measurement device 122 of the shape measurement unit 120 and the position of the marker 124 of the shape measurement unit 120. Therefore, the error attributable to the positional difference between the measurement device 122 and the marker 124 may be calibrated in order to accurately define the coordinate system. Accordingly, the processing unit 140 may individually acquire the coordinate transformation relationship between the marker 124 of the shape measurement unit 120 and the tracking sensor unit 130 and the coordinate transformation relationship between the measurement device 122 of the shape measurement unit 120 and the marker 124.

For example, the coordinate transformation relationships may be expressed as coordinate transformation matrices.

Hereinafter, the modeling setting and solving process of the optical tracking system 100 for defining the coordinate system of the patient 10 using the coordinate transformation relationships will be described in more detail with reference to the drawings.

Figure 2:
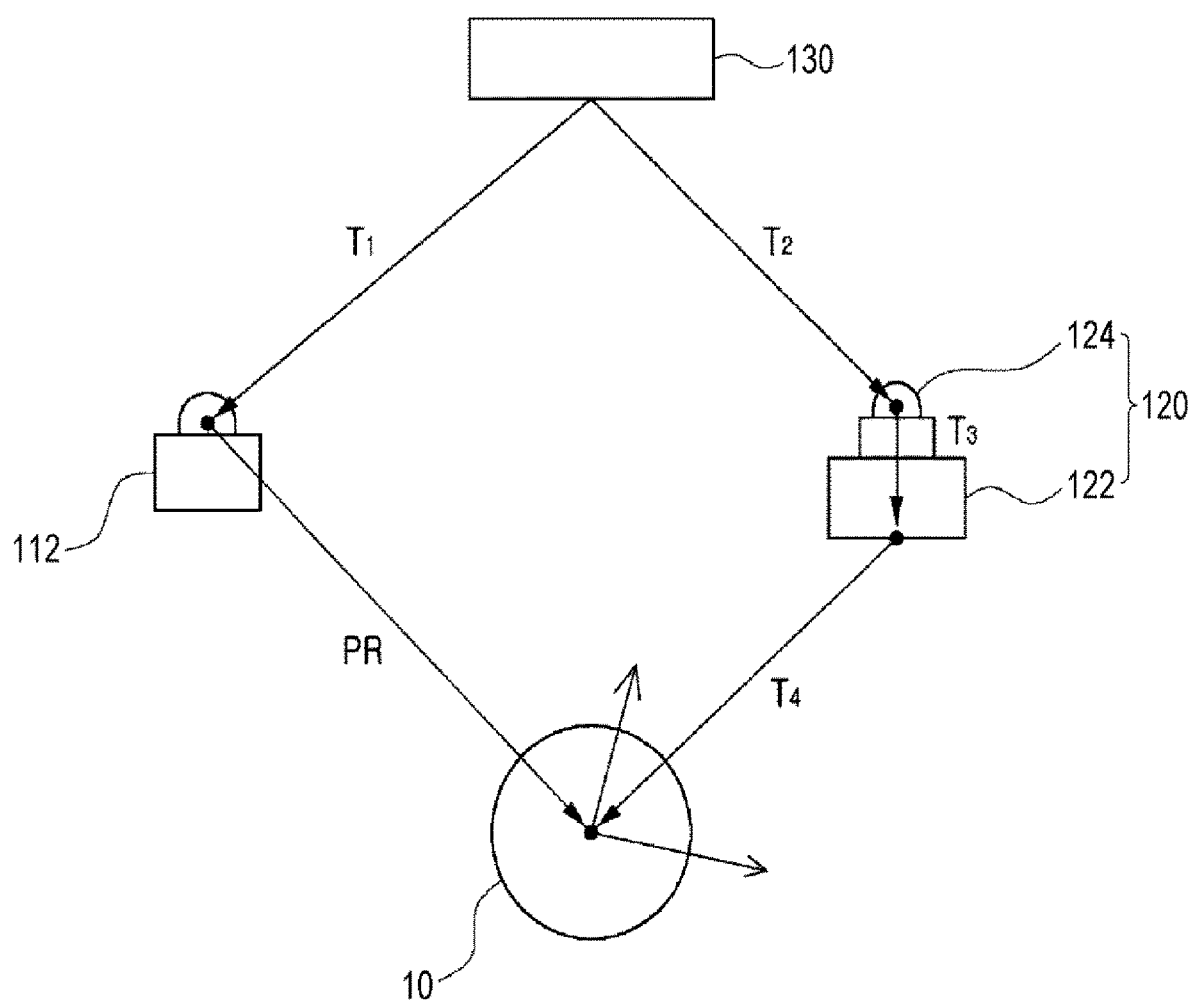
FIG. 2 is a conceptual diagram for explaining a modeling process of the optical tracking system shown in FIG. 1.

FIG. 2 is a conceptual diagram for explaining the modeling process of the optical tracking system shown in FIG. 1.

Referring to FIG. 2, the optical tracking system 100 may represent the coordinate transformation relationships as coordinate transformation matrices T1, T2, T3, T4, and PR.

Herein, PR refers to the coordinate transformation matrix of the patient 10 with respect to the reference marker unit 110. T1 refers to the coordinate transformation matrix of the reference marker unit 110 with respect to the tracking sensor unit 130. T2 refers to the coordinate transformation matrix of the marker 124 of the shape measurement unit 120 with respect to the tracking sensor unit 130. T3 refers to the coordinate transformation matrix of the measurement device 122 with respect to the marker 124 of the shape measurement unit 120. T4 refers to the coordinate transformation matrix of the patient 10 with respect to the measurement device 122 of the shape measurement unit 120.

If the coordinate transformation matrix PR of the patient 10 with respect to the reference marker unit 110 is represented by T1, T2, T3, and T4 based on the arrow directions shown in FIG. 2 so as to form a closed loop, formula 1 may be derived.

$$PR = T1^{-1} T2 T3 T4 \qquad \text{(Formula 1)}$$

On the other hand, two different paths from the tracking sensor unit 130 to the patient 10 are formed to make a closed loop, thereby deriving formula 2. Thereafter, by transforming formula 2, it is possible to derive formula 1 as the same result.

$$T1 PR = T2 T3 T4 \qquad \text{(Formula 2)}$$

The processing unit 140 may define the coordinate system of the patient 10 relative to the reference marker unit 110 by acquiring the coordinate transformation matrix PR by using formula 1 (or formula 2).

For example, the tracking sensor unit 130 may measure the information for acquiring the coordinate transformation matrix T1 of the reference marker unit 110 with respect to the tracking sensor unit 130 and the coordinate transformation matrix T2 of the marker of the shape measurement unit 120 with respect to the tracking sensor unit 130. The shape measurement unit 120 may measure the information for acquiring the coordinate transformation matrix T4 of the patient 10 with respect to measurement device of the shape measurement unit 120. The processing unit 140 may acquire the coordinate transformation matrices T1, T2, and T4 by using the measured information. The processing unit 140 may calculate the coordinate transformation matrix T3 of the measurement device 122 with respect to the marker 122 of the shape measurement unit 120 and the coordinate transformation matrix PR of the patient 10 with respect to the reference marker unit 110 from the acquired coordinate transformation matrices T1, T2, and T4.

Specifically, the coordinate transformation matrices T3 and PR may be acquired by applying the mathematical methods below. The processing unit 140 may calculate the coordinate transformation matrices T3 and PR by applying such mathematical methods.

First, the coordinate transformation matrices are formed so as to include a rotational transformation part R and a positional transformation part t. Thereafter, by substituting the coordinate transformation matrices into formula 2 and arranging the same, it is possible to derive formula 3.

$$\begin{bmatrix} R_{T1} & t_{T1} \\ 0 & 1 \end{bmatrix} \begin{bmatrix} R_{PR} & t_{PR} \\ 0 & 1 \end{bmatrix} = \begin{bmatrix} R_{T2} & t_{T2} \\ 0 & 1 \end{bmatrix} \begin{bmatrix} R_{T3} & t_{T3} \\ 0 & 1 \end{bmatrix} \begin{bmatrix} R_{T4} & t_{T4} \\ 0 & 1 \end{bmatrix} \qquad \text{(Formula 3)}$$

By arranging formula 3, it is possible to derive formula 4.

$$\begin{bmatrix} R_{T1} R_{PR} & R_{T1} t_{PR} + t_{T1} \\ 0 & 1 \end{bmatrix} - \begin{bmatrix} R_{T2} R_{T3} R_{T4} & R_{T2} R_{T3} t_{T4} + R_{T2} t_{T3} + t_{T2} \\ 0 & 1 \end{bmatrix} = 0 \qquad \text{(Formula 4)}$$

By expressing the respective components of formula 4 as an equation, formula 5 and formula 6 can be derived.

$$R_{T1} R_{PR} - R_{T2} R_{T3} R_{T4} = 0 \qquad \text{(Formula 5)}$$

$$R_{T1} t_{PR} + t_{T1} - R_{T2} R_{T3} t_{T4} - R_{T2} t_{T3} - t_{T2} = 0 \qquad \text{(Formula 6)}$$

By defining $R_{TT}$ in formula 5 and arranging formula 5, formula 7 can be derived.

$$R_{TT} R_{PR} - R_{T3} R_{T4} = 0, \quad R_{TT} = R_{T2}^{-1} R_{T1} \qquad \text{(Formula 7)}$$

Further, by additionally defining $t_{TT}$ in formula 6 and arranging formula 6, formula 8 can be derived.

$$R_{TT} t_{PR} - R_{T3} t_{T4} - t_{T3} = t_{TT}, \quad t_{TT} = R_{T2}^{-1} (t^{T2} - t^{T1}) \qquad \text{(Formula 8)}$$

In formulae 7 and 8, the rotational transformation matrix R has a form of 3×3 and the positional transformation matrix t has a form of 3×1. Thus, nine equations can be derived for the respective components of a 3×3 matrix from formula 7. In addition, three equations can be derived for the respective components of a 3×1 matrix from formula 8.

All the components of $R_{TT}$ (namely, all the components of $R_{T1}$ and $R_{T2}$) and all the components of $R_{T4}$ in formula 7 can be determined from the measurements described earlier. In addition, all the components of $t_{T4}$ can be determined in formula 8. Thus, there are altogether 24 unknown quantities including 9 components of each of $R_{PR}$ and $R_{T3}$ and 3 components of each of $t_{PR}$ and $t_{T4}$.

Formula 7 and formula 8 are 12 equations including 24 unknowns. Thus, it is possible to find more accurate values by performing the measurement two or more times. Accordingly, the measurement of the tracking sensor unit 130 and the shape measurement unit 120 may be performed two or more times.

Accordingly, the coordinate system of the patient 10 may be defined by using the coordinate transformation relationships measured as above.

The aforementioned mathematical method for acquiring the coordinate transformation matrices T3 and PR may be substituted by other methods. For example, the processing unit 140 may calculate the coordinate transformation matrices T3 and PR by using a dual quaternion method.

Specifically, formula 9 below may be derived from formula 1 described above and formula 10 below may be derived by transforming formula 9.

$$T1 PR - T2 T3 T4 = 0 \qquad \text{(Formula 9)}$$

$$(T1 + \varepsilon T1')(PR + \varepsilon PR') - (T2 + \varepsilon T2')(T3 + \varepsilon T3')(T4 + \varepsilon T4') = 0 \qquad \text{(Formula 10)}$$

By developing formula 10 and eliminating a high-order term, formula 11 below can be derived.

$$T1 PR' + T1' PR - T2 T3 T4' - T2 T3' T4 - T2' T3 T4 = 0 \qquad \text{(Formula 11)}$$

By transforming formula 9 and formula 11 by using a dual quaternion method, formula 12 and formula 13 below can be derived.

$$\widetilde{T1}\,\widetilde{PR} - \widetilde{T2T4}\,\widetilde{T3} = 0 \qquad \text{(Formula 12)}$$

$$\widetilde{T1}'\widetilde{PR} + \widetilde{T1}\widetilde{PR}' - (\widetilde{T2T4}'' + \widetilde{T2'T}\,4)\widetilde{T3} - \widetilde{T2T4}\widetilde{T3}' = 0 \qquad \text{(Formula 13)}$$

By transforming formula 12 and formula 13 into the form of a matrix equation, formula 14 below can be derived and the coordinate transformation matrices T3 and PR may be calculated from formula 14.

$$\begin{bmatrix} \widetilde{T1} & 0 & -\widetilde{T2T4} & 0 \\ \widetilde{T1}'\,\widetilde{T1} & -(\widetilde{T2T4}'' + \widetilde{T2'T4}) & -\widetilde{T2T4} \end{bmatrix} \begin{bmatrix} \widetilde{PR} \\ \widetilde{PR}' \\ \widetilde{T3} \\ \widetilde{T3}' \end{bmatrix} = 0 \qquad \text{(Formula 14)}$$

Meanwhile, the processing unit 140 may register the coordinate system of the three-dimensional image acquired in advance before surgical treatment for the patient 10 with the coordinate system of the patient 10 defined relative to the reference marker unit 110, based on the three-dimensional shape measured in the shape measurement unit 120.

Specifically, instead of directly attaching a marker or a structure corresponding to the marker to the patient 10 and registering the coordinate system of the three-dimensional image with the coordinate system of the patient based thereon, the coordinate system of the three-dimensional shape acquired as above (or the three-dimensional image obtained therefrom) and the coordinate system of the three-dimensional image are registered by using the three-dimensional shape itself as a marker (a natural landmark).

In this manner, the processing unit 140 may define the coordinate system of the patient 10 relative to the reference marker unit 110 from the coordinate transformation relationships and may track the patient 10 in real time during surgical treatment.

The process of defining the coordinate system of the patient 10 relative to the reference marker unit 110 may be automatically or manually re-performed with ease. That is, the processing unit 140 may automatically or manually re-define the coordinate system of the patient 10 when the patient 10 moves. At this time, even when the patient 10 does not actually move, if the distance between the patient 10 and the reference marker unit 110 changes, it may be regarded as a case where the patient 10 moves.

The process of defining the coordinate system of the patient 10 relative to the reference marker unit 110 by the processing unit 140 may be automatically or manually re-performed with ease.

Accordingly, when the patient 10 moves or the posture thereof changes, the coordinate system may be accurately reset by re-performing the process of defining the coordinate system (acquisition of a changed PR).

In one embodiment, the optical tracking system 100 may include a motion sensing unit (not shown) configured to sense a motion of the patient 10. Further, instead of separately using the motion sensing unit, the motion of the patient 10 may be sensed by the tracking sensor unit 130. When the motion of the patient 10 is sensed by the motion sensing unit or the tracking sensor unit 130, the processing unit 140 may reset the coordinate system by re-performing the process of defining the coordinate system.

Accordingly, the coordinate system of the patient 10 relative to the reference marker unit 110 may be defined in real time. Thus, even when the patient moves or the posture thereof changes during surgical treatment, it is possible to accurately track the patient 10 in real time.

Furthermore, the registration can be performed by using, as a marker, the three-dimensional shape itself measured during surgical treatment. Thus, even without directly attaching the DRB such as a marker or a structure corresponding to the marker to the patient 10, the coordinate system of the three-dimensional image acquired in advance before surgical treatment can be registered with the coordinate system of the patient 10 who may move in real time during surgical treatment. In addition, even when acquiring the three-dimensional image in advance, there is no need to attach the DRB. Since the resetting and re-registration of the coordinate systems can be performed at any time, it is not necessary to strictly fix the reference marker unit 110 to the patient 10.

Accordingly, it is possible to solve the problems in the related art, such as the pain experienced by the patient and an error due to directly attaching the marker to the patient, the onerous work of manufacturing the STAMP before a surgery, substantial time and cost required in manufacturing the STAMP, and etc. That is, the setting of the coordinate system of the patient and the registration of the images can be expeditiously performed in an operating room without a separate preparation process. Thus, it is possible to accurately and easily perform the setting of the coordinate system of the patient and the registration of the images in a shorter time and with a reduced cost. Further, the operation to the patient may be performed without the DRB that would otherwise be attached directly to the patient. Thus, it is possible to alleviate the pain of the patient and side effects.

Figure 3:
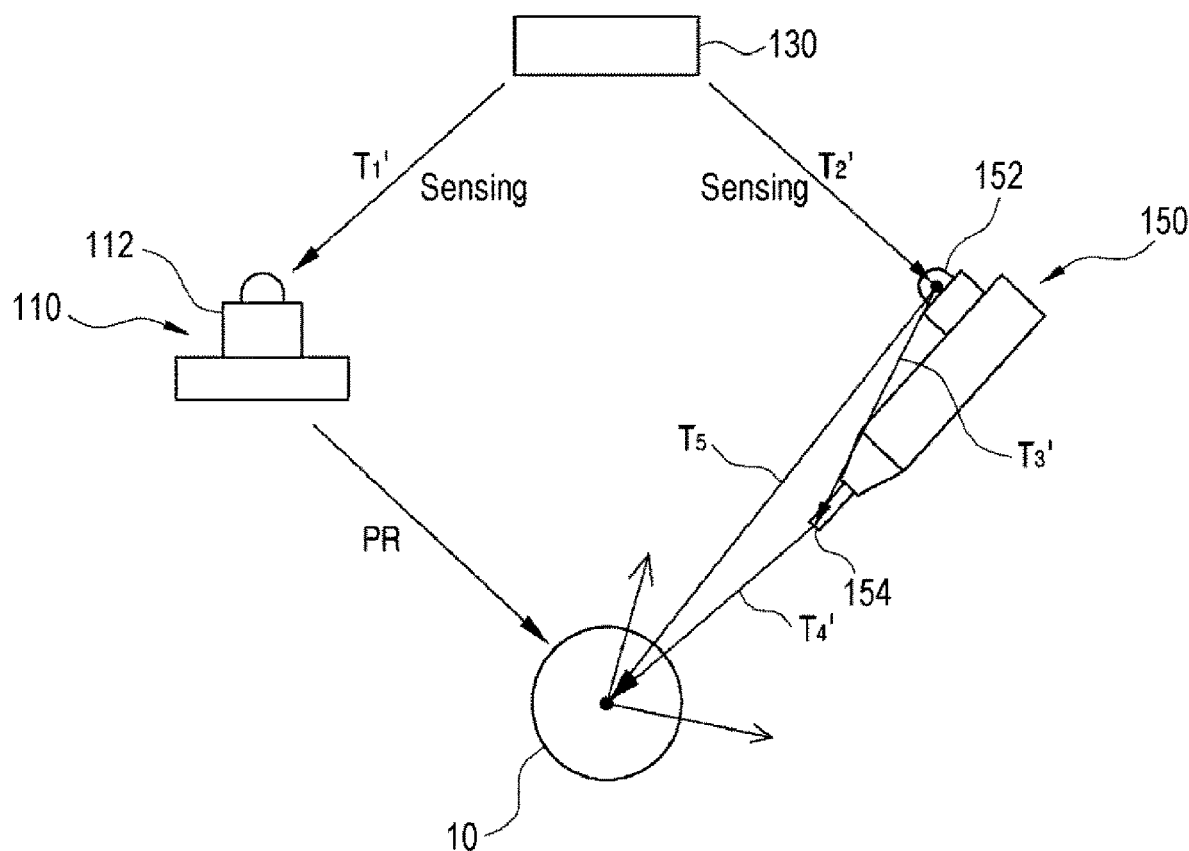
FIG. 3 is a conceptual diagram for explaining tracking of a surgical instrument and registration in the optical tracking system shown in FIG. 1.

FIG. 3 is a conceptual diagram for explaining the tracking and registration of a surgical instrument in the optical tracking system shown in FIG. 1.

Referring to FIG. 3, the optical tracking system 100 may further include a surgical instrument 150.

The surgical instrument 150 is an instrument for surgically treating the patient 10 and includes a marker 152. The marker 152 and the marker 112 are capable of radiating energy or a signal so that the energy or the signal can be sensed by the tracking sensor unit 130. For example, the marker 152 may be formed in a plural number and may include pattern information.

The tracking sensor unit 130 may track the surgical instrument 150 by sensing the marker 152 of the surgical instrument 150.

The processing unit 140 acquires the coordinate transformation relationship between the reference marker unit 110 and the tracking sensor unit 130 and the coordinate transformation relationship between the marker 152 of the surgical instrument 150 and the tracking sensor unit 130 based on the sensing result of the tracking sensor unit 130. Herein, the coordinate transformation relationships may be defined, for example, in the form of a matrix and may be expressed as coordinate transformation matrices.

The processing unit 140 may define a coordinate system of the surgical instrument 150 relative to the patient 10 by using the coordinate transformation relationships acquired above and the coordinate system of the patient 10 relatively defined with respect to the reference marker unit 110. For example, the coordinate system may be defined in the form of a matrix.

The reference marker unit 110 is stationarily disposed relative to the patient 10. Thus, it is possible to use the coordinate system of the patient 10 relatively defined with respect to the reference marker unit 110 described above with reference to FIGS. 1 and 2. That is, by using the coordinate transformation matrix PR of the patient 10 with respect to the reference marker unit 110 and by using the coordinate transformation matrices T1' and T2' sensed and calculated by the tracking sensor unit 130, it is possible to determine the coordinate transformation matrix T5 of the surgical instrument 150 relatively defined with respect to the patient 10 according to the following formula 15 transformed from formula 1 and formula 2.

$$PR = T1'^{-1}T2'T5, \quad T1'PR = T2'T5 \qquad \text{(Formula 15)}$$

Accordingly, the coordinate system of the surgical instrument 150 relative to the patient 10 may be defined by using the coordinate transformation relationships measured as above.

In FIG. 3 and formula 15, the coordinate transformation matrix T5 of the surgical instrument 150 is shown on the basis of the marker 152. However, the coordinate transformation matrix T5 may also be defined on the basis of a point to be tracked, for example, an end portion 154 of the surgical instrument 150. That is, the coordinate transformation matrix T5 may be defined by using the coordinate transformation matrix T3' of the end portion 154 with respect to the marker 152 of the surgical instrument 150 and the coordinate transformation matrix T4' of the patient 10 with respect to the end portion 154 of the surgical instrument 150 (T5=T3'T4'). In this case, T3' may be determined from the geometric shape of the surgical instrument 150. Thus, the coordinate system of the surgical instrument 150 relative to the patient 10 may be defined on the basis of the end portion 154.

In the meantime, the processing unit 140 may register the coordinate system of the three-dimensional image acquired in advance before surgical treatment for the patient 10 with the coordinate system of the surgical instrument 150 relatively defined with respect to the patient 10, based on the registration result of the coordinate system of the three-dimensional image and the coordinate system of the patient 10.

That is, as described with reference to FIGS. 1 and 2, the coordinate system of the three-dimensional image acquired in advance before surgical treatment for the patient 10 and the coordinate system of the patient 10 relatively defined with respect to the reference marker unit 110 may be registered based on the three-dimensional shape measured in the shape measurement unit 120. As described above, the coordinate system of the surgical instrument 150 relative to the patient 10 may be defined. Accordingly, the coordinate system of the three-dimensional image acquired in advance before surgical treatment for the patient 10 and the coordinate system of the surgical instrument 150 relatively defined with respect to the patient 10 may be registered with each other.

The optical tracking system 100 may further include a display unit (not shown) connected to the processing unit 140. The display unit may display the three-dimensional image acquired in advance before surgical treatment, the image for the three-dimensional shape measured in the shape measurement unit 120, an image for the surgical instrument 150, an overlapped image of the aforementioned images registered with each other, etc.

In this manner, the processing unit 140 may define the coordinate system of the surgical treatment relative to the patient 10 from the coordinate transformation relationships and may track the surgical instrument 150 in real time during surgical treatment.

The process of defining the coordinate system of the patient 10 relative to the reference marker unit 110 may be automatically or manually re-performed with ease. That is, the processing unit 140 may automatically or manually re-define the coordinate system of the patient 10 when the patient 10 moves. At this time, even when the patient 10 does not actually move, if the distance between the patient 10 and the reference marker unit 110 changes, it may be deemed as a case where the patient 10 moves.

Accordingly, when the patient 10 moves or the posture thereof changes, the coordinate system may be accurately reset by re-performing the process of defining the coordinate system (acquisition of a changed PR). Furthermore, the processing unit 140 may reset the coordinate system of the surgical instrument 150 relative to the patient 10 and may track the surgical instrument 150 in real time during surgical treatment.

As a result, since the coordinate system of the patient 10 relative to the reference marker unit 110 may be defined in real time, even when the patient moves or the posture thereof changes during surgical treatment, the surgical instrument 150 may be accurately tracked in real time.

Further, even without directly attaching the DRB, such as a marker or a structure corresponding to the marker, to the patient 10, the coordinate system of the three-dimensional image acquired in advance before surgical treatment can be registered with the coordinate system of the surgical instrument 150 which may move in real time during surgical treatment. In addition, even when acquiring the three-dimensional image in advance, there is no need to attach the DRB and since the resetting and re-matching of the coordinate systems can be performed at any time, it is not necessary to strictly fix the reference marker unit 110 to the patient 10.

Accordingly, the problems in the related art, such as the pain experienced by the patient and an error due to directly attaching the marker to the patient, the onerous work of manufacturing the STAMP before a surgery, substantial time and cost required in manufacturing the STAMP, etc., may be solved. That is, because the setting of the coordinate system of the surgical instrument and the image registration can be expeditiously performed in an operating room without a separate preparation process, the setting of the coordinate system of the surgical instrument and the registration of the images can be performed accurately and easily in a shorter time and with a reduced cost. Further, the operation to the patient may be performed without the DRB that would otherwise be directly attached to the patient. Thus, the pain of the patient and the side effects may be alleviated.

Hereinafter, a process of registering the coordinate system of the three-dimensional image captured in advance before surgical treatment with the coordinate system of the actual world during surgical treatment where the lesion of the patient and the surgical instrument are positioned, by using the optical tracking system 100, will be described with reference to the drawings.

Figure 4:
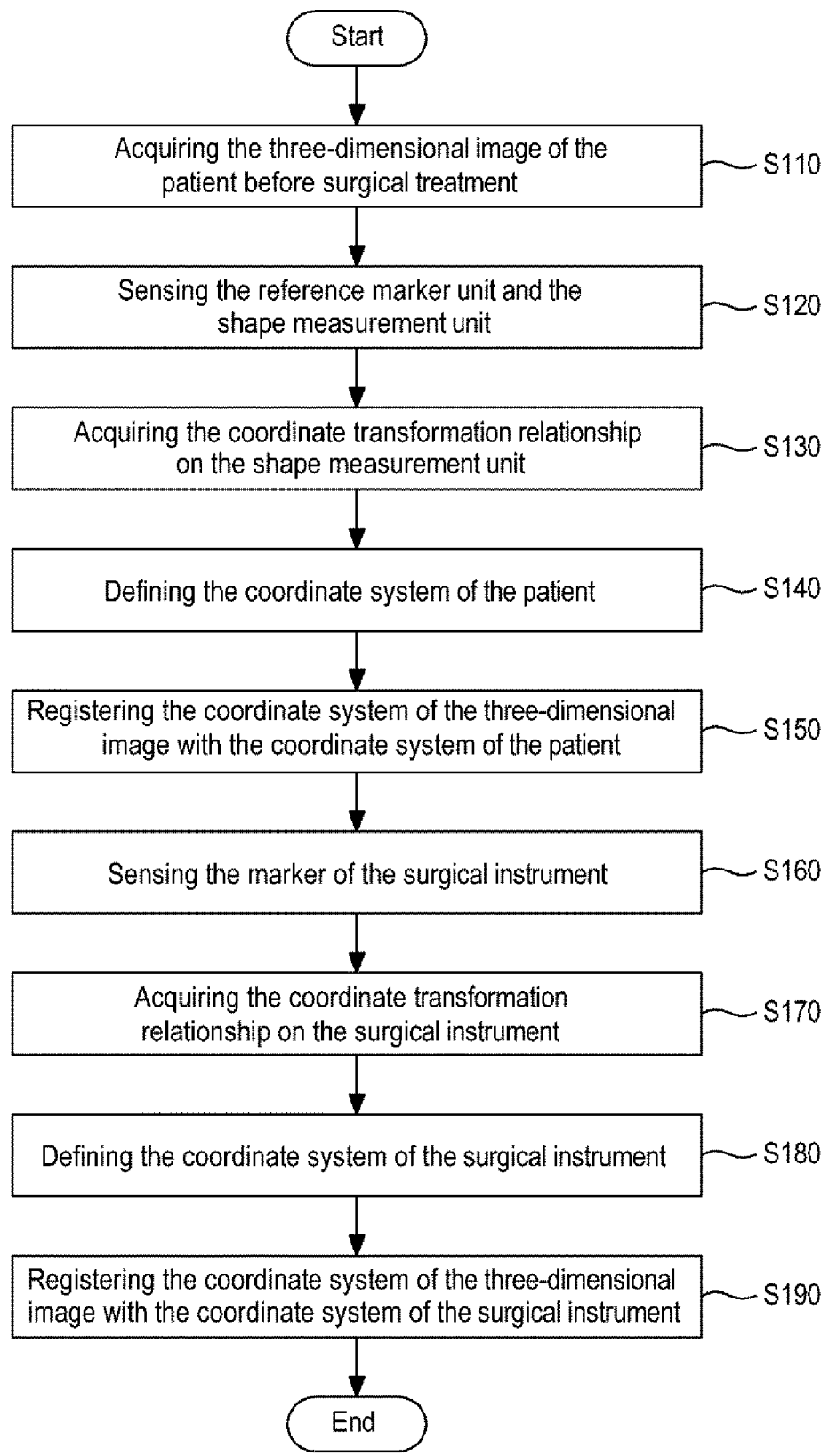
FIG. 4 is a flowchart showing a coordinate registration method for an optical tracking system according to one embodiment of the present disclosure.

FIG. 4 is a flowchart showing a coordinate registration method for an optical tracking system according to one embodiment of the present disclosure.

Referring to FIGS. 1 to 4, a three-dimensional image, for example, a CT image, of the patient 10 is first acquired before surgical treatment for the patient 10 (S110).

The three-dimensional image such as a CT image or the like (including the reconstructed image thereof) acquired in advance before surgical treatment in the aforementioned manner may be stored in, for example, a computer.

Then, the surgical treatment procedures are performed in the following manner.

First, the reference marker unit 110 stationarily disposed relative to the patient 10 and the shape measurement unit 120 configured to measure the three-dimensional shape of the specified part of the patient 10 corresponding to the three-dimensional image are sensed by the tracking sensor unit 130 (S120).

Next, the coordinate transformation relationship between the reference marker unit 110 and the tracking sensor unit 130 and the coordinate transformation relationship between the shape measurement unit 120 and the tracking sensor unit 130 are acquired based on the sensing result of the tracking sensor unit 130, and the coordinate transformation relationship between the specified part of the patient 10 and the shape measurement unit 120 is acquired based on the measurement result of the shape measurement unit 120 (S130).

At this time, the coordinate transformation relationship between the reference marker unit 110 and the tracking sensor unit 130 and the coordinate transformation relationship between the marker of the shape measurement unit 120 and the tracking sensor unit 130 are acquired, the coordinate transformation relationship between the measurement device 122 of the shape measurement unit 120 and the marker 124 is acquired, and the coordinate transformation relationship between the patient 10 and the measurement device 122 of the shape measurement unit 120 may be acquired.

Then, the coordinate system of the patient 10 relative to the reference marker unit 110 is defined from the coordinate transformation relationships acquired as above (S140).

Next, the coordinate system of the three-dimensional image acquired above and the coordinate system of the patient 10 defined above may be registered based on the three-dimensional shape measured in the shape measurement unit 120 (S150).

In this manner, the coordinate system of the patient 10 may be relatively defined with respect to the reference marker unit 110, and the coordinate system of the three-dimensional image such as a CT image or the like acquired in advance may be registered with the coordinate system of the patient 10.

The surgical instrument 150 having the marker 152 attached thereto is provided to a surgical operator such as a doctor. The surgical operator operates the surgical instrument 150 for surgically treating the patient 10, either directly or through the use of equipment such as a surgical robot or the like. The following tracking procedures are performed with respect to the surgical instrument 150.

The tracking sensor unit 130 senses the marker 152 of the surgical instrument 150 (S160).

Then, the coordinate transformation relationship between the reference marker unit 110 and the tracking sensor unit 130 and the coordinate transformation relationship between the marker 152 of the surgical instrument 150 and the tracking sensor unit 130 are acquired based on the sensing result of the tracking sensor unit 130 (S170).

Next, the coordinate system of the surgical instrument 150 relative to the patient 10 is defined by using the coordinate transformation relationships acquired above and the coordinate system of the patient 10 relatively defined with respect to the reference marker unit 110 (S180).

Then, the coordinate system of the three-dimensional image acquired above and the coordinate system of the surgical instrument 150 defined above are registered based on the registration result of the coordinate system of the three-dimensional image and the coordinate system of the patient 10 (S190).

In this manner, the coordinate system of the surgical instrument 150 for surgically treating the patient 10 is relatively defined with respect to the patient 10, and the coordinate system of the three-dimensional image such as a CT image or the like acquired in advance may be registered with the coordinate system of the surgical instrument 150.

When the patient 10 moves, the coordinate system of the patient 10 may be re-defined automatically or manually. Thus, the step S120 of sensing the shape measurement unit 120 by the tracking sensor unit 130 and the subsequent steps may be repeated. At this time, even when the patient 10 does not actually move, if the distance between the patient 10 and the reference marker unit 110 changes, it may be considered as a case where the patient 10 moves.

In the present embodiment, the coordinate system registration method for the optical tracking system 100 has been briefly described with reference to the flowchart of FIG. 4. However, because the specific operations of the optical tracking system 100 are substantially the same as those described earlier with reference to FIGS. 1 to 3, detailed descriptions that are duplicative will be omitted.

According to the present disclosure, the optical tracking system includes the shape measurement unit configured to measure the three-dimensional shape of the specified part of the patient. The shape measurement unit and the reference marker unit are sensed by the tracking sensor unit. Thus, the coordinate system of the patient relative to the reference marker unit can be defined from the coordinate transformation relationships among the shape measurement unit, the reference marker unit, and the tracking sensor unit, and during surgical treatment, it is possible to track the patient and the surgical instrument in real time.

Further, the process of defining the coordinate system of the patient relative to the reference marker unit can be re-performed with ease. Therefore, even when the patient moves or the posture thereof changes, the coordinate system may be accurately reset and the patient and the surgical instrument may be accurately tracked in real time.

Furthermore, since the registration can be performed by using, as a marker, the three-dimensional shape of the patient measured during surgical treatment, even without directly attaching the DRB to the patient, the coordinate system of the three-dimensional image acquired in advance before surgical treatment can be registered with the coordinate system of the patient and the coordinate system of the surgical instrument which may move in real time during surgical treatment. In addition, even when acquiring the three-dimensional image in advance, there is no need to attach the DRB. Further, because the resetting and re-registration of the coordinate systems can be performed at any time, it is not necessary to strictly fix the reference marker unit to the patient.

Accordingly, the problems in the related art, such as the pain experienced by the patient or an error due to directly attaching the marker to the patient, the onerous work of manufacturing the STAMP before a surgery, substantial time and cost required in manufacturing the STAMP, etc., may be solved.

That is, the setting of the coordinate system of the patient and the image registration can be expeditiously performed in an operating room without a separate preparation process. It is therefore possible to accurately and easily perform the setting of the coordinate system of the patient and the coordinate system of the surgical instrument and the image registration in a shorter time and with a reduced cost. Further, the operation to the patient may be performed without the DRB that would otherwise be directly attached to the patient. Thus, the pain of the patient and side effects can be alleviated.

While the present disclosure has been described above with reference to the preferred embodiments, a person skilled in the relevant technical field or a person having ordinary knowledge in the relevant technical field will be able to diversely modify or change the present disclosure without departing from the spirit and technical scope of the present disclosure defined in the appended claims. Accordingly, it shall be construed that the foregoing descriptions and the accompanying drawings are not intended to limit the technical idea of the present disclosure but are intended to illustrate the present disclosure.

(DESCRIPTION OF REFERENCE NUMERAL)

| 100: optical tracking system | 110: reference marker unit |
| 120: shape measurement unit | 130: tracking sensor unit |
| 140: processing unit | 150: surgical instrument |

What is claimed is:

1. An optical tracking system for tracking a patient or a surgical instrument for surgically treating the patient by using a three-dimensional image acquired in advance before surgical treatment for the patient, comprising:
 a reference marker unit fixedly attached to an object that is stationarily disposed relative to the patient and spaced apart from the patient;
 a shape measurement device including a measurement device and a marker installed on the measurement device, and configured to measure a three-dimensional shape of a specified part of the patient corresponding to the three-dimensional image;
 a tracking sensor configured to sense the reference marker unit and the shape measurement device so as to track the reference marker unit and the shape measurement device, respectively; and
 a processing unit configured to:
  acquire a coordinate transformation relationship between the reference marker unit and the tracking sensor and a coordinate transformation relationship between the shape measurement device and the tracking sensor based on a sensing result of the tracking sensor,
  acquire a coordinate transformation relationship between the specified part of the patient and the shape measurement device based on a measurement result of the shape measurement device, and
  define a coordinate system of the patient relative to the reference marker unit from the acquired coordinate transformation relationships,
 wherein the processing unit is further configured to register a coordinate system of the three-dimensional image acquired in advance before the surgical treatment for the patient with the coordinate system of the patient relatively defined with respect to the reference marker unit, based on the three-dimensional shape measured in the shape measurement device, and
 wherein the optical tracking system further comprises a surgical instrument including a marker and configured to surgically treat the patient,
 wherein the tracking sensor is further configured to sense the marker of the surgical instrument so as to track the marker of the surgical instrument, and
 wherein the processing unit is further configured to acquire a coordinate transformation relationship between the reference marker unit and the tracking sensor and a coordinate transformation relationship between the marker of the surgical instrument and the tracking sensor based on a sensing result of the tracking sensor and to define a coordinate system of the surgical instrument relative to the patient by using the acquired coordinate transformation relationships and the coordinate system of the patient relatively defined with respect to the reference marker unit.

2. The optical tracking system according to claim 1, wherein the processing unit is configured to acquire a coordinate transformation relationship between the marker of the shape measurement device and the tracking sensor and a coordinate transformation relationship between the measurement device of the shape measurement device and the marker of the shape measurement device.

3. The optical tracking system according to claim 2, wherein the coordinate transformation relationships are expressed as coordinate transformation matrices, and
 wherein the processing unit is configured to define the coordinate system of the patient relative to the reference marker unit according to the following mathematical formula:

$$PR = T1^{-1} T2 T3 T4$$

where PR is a coordinate transformation matrix of the patient with respect to the reference marker unit, T1 is a coordinate transformation matrix of the reference marker unit with respect to the tracking sensor, T2 is a coordinate transformation matrix of the marker of the shape measurement device with respect to the tracking sensor, T3 is a coordinate transformation matrix of the measurement device of the shape measurement device with respect to the marker of the shape measurement device, and T4 is a coordinate transformation matrix of the patient with respect to the measurement device of the shape measurement device.

4. The optical tracking system according to claim 3, wherein the tracking sensor is configured to measure information for acquiring the coordinate transformation matrix T1 of the reference marker unit with respect to the tracking sensor and the coordinate transformation matrix T2 of the marker of the shape measurement device with respect to the tracking sensor, wherein the shape measurement device is configured to measure information for acquiring the coordinate transformation matrix T4 of the patient with respect to the measurement device of the shape measurement device, and
 wherein the processing unit is configured to acquire the coordinate transformation matrices T1, T2, and T4 using the measured information and to calculate, from the acquired coordinate transformation matrices T1, T2, and T4, the coordinate transformation matrix T3 of the measurement device of the shape measurement device with respect to the marker of the shape measurement device and the coordinate transformation matrix PR of the patient with respect to the reference marker unit.

5. The optical tracking system according to claim 4, wherein the measurement of the tracking sensor and the shape measurement device is performed two or more times.

6. The optical tracking system according to claim 1, wherein the processing unit is configured to register the coordinate system of the three-dimensional image acquired in advance before the surgical treatment for the patient with the coordinate system of the surgical instrument relatively defined with respect to the patient, based on a registration result of the coordinate system of the three-dimensional image and the coordinate system of the patient.

7. The optical tracking system according to claim 1, wherein the processing unit is configured to automatically or manually re-define the coordinate system of the patient when the patient moves.

* * * * *